United States Patent

Kwiatkowski et al.

Patent Number: 5,728,881
Date of Patent: Mar. 17, 1998

[54] PROCESS FOR PREPARING TRIFLURALIN

[75] Inventors: Stefan Kwiatkowski; Krzysztof Pupek; Miroslaw J. Golinski, all of Richmond, Ky.; Paul D. Smith, League City, Tex.; Lowell J. Lawrence, Richmond, Ky.

[73] Assignee: SRM Chemical, Ltd. Co., League City, Tex.

[21] Appl. No.: 810,883

[22] Filed: Mar. 5, 1997

[51] Int. Cl.$^6$ .................................................. C02C 209/10
[52] U.S. Cl. ............................................. 564/406; 564/437
[58] Field of Search ........................................ 564/406, 437

[56] References Cited

U.S. PATENT DOCUMENTS

| | | |
|---|---|---|
| 3,257,190 | 6/1966 | Soper . |
| 3,403,180 | 9/1968 | Soper . |
| 4,078,000 | 3/1978 | Gavin et al. . |
| 4,120,905 | 10/1978 | Cannon et al. . |
| 4,127,610 | 11/1978 | Eizember et al. . |
| 4,185,035 | 1/1980 | Eizember et al. . |
| 4,226,789 | 10/1980 | Eizember et al. . |
| 4,335,260 | 6/1982 | Bornengo et al. . |
| 4,338,473 | 7/1982 | Habig et al. . |
| 4,440,962 | 4/1984 | Pallucca . |
| 4,501,608 | 2/1985 | Cannon . |
| 4,638,090 | 1/1987 | Heinrich et al. . |
| 4,675,445 | 6/1987 | Davis et al. . |
| 4,874,895 | 10/1989 | Graziello . |
| 4,876,388 | 10/1989 | Ravetta . |
| 4,970,343 | 11/1990 | Pikarski et al. . |
| 5,196,585 | 3/1993 | Wirth . |

*Primary Examiner*—Brian M. Burn
*Attorney, Agent, or Firm*—King & Schickli

[57] ABSTRACT

A process is provided for preparing 2,6-dinitro-N,N-dipropyl-4-(trifluoromethyl)benzenamine from 4-chlorotrifluoromethylbenzene. The process includes a two stage nitration and an amination step. Ethylene dichloride is utilized as a diluent and solvent in the nitration steps. Spent acid from the first nitration is reconstituted with sulfur trioxide for use in the second nitration. Spent acid from the second nitration is used directly in the first nitration and evaporation is used to remove nitrosoamines from the final trifluralin product.

11 Claims, No Drawings

PROCESS FOR PREPARING TRIFLURALIN

TECHNICAL FIELD

The present invention relates generally to a process for the production for 2,6-dinitro-N,N-dipropyl-4-(trifluoromethyl) benzenamine, also known as trifluralin from 4-chlorotrifluoromethylbenzene.

BACKGROUND OF THE INVENTION 2,6-dinitro-N,N-dipropyl-4-(trifluoromethyl) benzenamine or trifluralin has long been known to be useful as a herbicide for eliminating germinating and seedling weed grasses and selected broad leaf weeds. Processes for the preparation of trifluralin are disclosed in, for example, U.S. Pat. Nos. 3,257,190 and 3,403,180 both to Soper.

One of the by-products of trifluralin production is nitrosoamine formation. In fact, nitrosoamine may be present as a by-product in trifluralin production at concentrations of up to 250 parts/million (ppm). Nitrosoamines are known carcinogens and are considered dangerous for warm-blooded animals and, particularly, for man. Accordingly, laws have been passed in various countries to put limits on the permissible concentration of nitrosoamines in herbicides. In fact, nitrosoamines are so dangerous, the United States government limits nitrosoamines concentrations in herbicides to one ppm.

In order to meet this requirement, a number of methods or processes have been developed for purifying dinitroaniline herbicides such as trifluralin and thereby reducing the concentration of the undesired nitrosoamines to below the one ppm federal limit. Most purification schemes rely upon reaction of the formed nitrosoamines or precursors of the nitrosoamines with various chemical reagents including but not limited to hydrochloric acid, sulfonic acid, carboxylic acid halides, hydrobromic acid, sulfamic acid, hydrobromide salts and alkali metal and/or ammonium bisulfite. These chemical purification methods are disclosed in various patents including, for example, U.S. Pat. Nos. 4,120,905 to Cannon et al.; 4,127,610 to Eizember; 4,185,035 to Eizember et al.; 4,226,789 to Eizember et al.; 4,335,260 to Bornengo et al.; 4,440,962 to Pallucca; 4,501,608 to Cannon; 4,638,090 to Heinrich et al.; 4,675,445 to Davis et al.; and 4,874,895 to Graziello; 4,970,343 to Pikarski et al. and 5,196,585 to Wirth.

Generally, these chemical processes suffer from a number of disadvantages. Many of the chemical reagents required are expensive and/or require special handling or specialized equipment. Many of these processes also result in undesired trifluralin yield reductions and/or undesired by-products requiring special handling or processing prior to environmental disposal. Further, many of the purification procedures are overly time consuming thereby significantly adding to the production cost.

Recognizing these and other shortcomings of the various chemical purification processes, physical purification processes have also been developed. These are generally disclosed in U.S. Pat. Nos. 4,338,473 to Habig et al. and 4,876,388 to Ravetta. In the Habig et al. patent, in order to remove nitrosoamines forming precursor, the water steam is blown through melted 4-chloro-3,5-dinitrobenzotrifluoride (the trifluralin precursor) prior to the final amination step of the trifluralin production process. In contrast, in the Ravetta patent, crude trifluralin is subjected to steam distillation in order to remove the formed nitrosoamines. While both of these physical processes for purifying trifluralin and removing nitrosoamines are effective, it should be appreciated that still further improvement in the process of efficiently and economically producing trifluralin is possible.

SUMMARY OF THE INVENTION

Accordingly, it is a primary object of the present invention to provide a process for preparing trifluralin overcoming the above described limitations and disadvantages of the prior art.

Still another object of the present invention is to provide a process for the preparation of trifluralin in a more cost effective manner by significantly reducing by-product production, allowing recycling of solvents and reagents and also removing nitrosoamines by-products thereby resulting in a more purified, high yield trifluralin product.

Yet another object of the present invention is to provide a process for preparing trifluralin wherein a first stage nitration mixture is extracted utilizing an organic solvent. This allows recovery of product without addition of water. The addition of water to recover product as taught in the prior art adds significantly to production costs since water must be converted back to sulfuric acid through the addition of sulfur trioxide if the acid stream is to be recycled. In contrast, if the acid stream is disposed of, economic and environmental costs are even higher due to the fact that such costs are generally related to the volume of material in the waste stream.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, a process is provided for producing or preparing 2,6-dinitro-N,N-dipropyl-4 -(trifluoromethyl) benzenamine (trifluralin) from 4-chlorotrifluoromethylbenzene. The process includes a step of mononitrating 4-chlorotrifluoromethylbenzene substantially completely to 4-chloro-3-nitrotrifluoromethylbenzene with a mixture of nitric acid and oleum. Next is the step of separating the 4-chloro-3-nitrotrifluoromethylbenzene from the waste acid mixture. This is done by adding ethylene dichloride. This is then followed by the step of dinitrating the 4-chloro-3-nitrobenzotrifluoromethylbenzene with a fresh mixture of nitric acid and oleum. Then is the step of separating the 4-chloro-3,5-dinitrotrifluoromethyl benzene from the mixture of nitric acid and oleum. Following this step is the amination of the 4-chloro-3,5-dinitrotrifluoromethylbenzene with dipropylamine to produce 2,6-dinitro-N,N-dipropyl-4-(trifluoromethyl) benzenamine.

More specifically describing the process, after the ethylene dichloride is added as a solvent to separate the 4-chloro-3,5-dinitrotrifluoromethylbenzene from the waste acid mixture, there is the step of distilling of the ethylene dichloride. The ethylene dichloride is then collected and recycled or reused in the separating step of the next batch being processed. Further, the method includes the evaporating of the volatile components directly from the 2,6-dinitro-N,N-dipropyl-4-(trifluoromethyl) benzenamine, produced during the aminating step.

Advantageously, the present process for the production of trifluralin is characterized by a number of distinct advantages. By using ethylene dichloride as a diluent and a solvent in the first or mononitration step, the nitration may be performed with a more concentrated nitration mixture. Accordingly, the reaction is faster and the formation of any 4-chlorobenzoic acid by-product as a result of the hydrolysis of the substrate is substantially eliminated. Further, the use of ethylene dichloride eliminates the necessity of diluting the post nitration mixture with water in accordance with the prior art procedure disclosed in U.S. Pat. No. 4,096,195 to Schneider et al. As a result, no special equipment for cooling is necessary. Further, no diluted sulfuric acid waste is generated and in fact, the sulfuric acid produced in the present process is substantially 100% free of organic impurities. Accordingly, the sulfuric acid may be enriched with $SO_3$ to produce oleum which may then be recycled as a starting material in the dinitrating step. As already mentioned, this reduces the economic costs of acid feedstocks as well as the economic and environmental costs associated with waste acid disposal. This can also significantly reduce capital investment in equipment for completing the process and the cost of processing as well.

The present process also represents a significant advantage over the steam distillation process for removing nitrosoamines by-products as set forth in U.S. Pat. No. 4,876,388 to Ravetta. Specifically, in the present process it is not necessary to separate the crude trifluralin from waste water, following the amination step. This represents a significant savings in processing time and also reduces the needed processing equipment. Additionally, it eliminates one waste water treatment step from the process. Further, since saturated water steam is not utilized, capital expenditure for steam production equipment is not necessary and in fact, the processing reactor may be of more simplified design to provide simpler operation. The present method also allows dipropylamine to be collected as a first condensate. This dipropylamine may then be recycled and, therefore, the present process effectively minimizes raw material waste and, therefore, is more economical to complete.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

DETAILED DESCRIPTION OF THE INVENTION

The present process for the preparation of 2,6-dinitro-N, N-dipropyl-4-(trifluoromethyl)benzenamine or trifluralin from 4-chlorotrifluoromethylbenzene, a readily available starting material, includes an initial two stage nitration. In the initial step, 4-chlorotrifluoromethylbenzene is substantially completely mononitrated to 4-chloro-3-nitrotrifluoromethylbenzene with a mixture of nitric acid and oleum ($H_2SO_4/SO_3$).

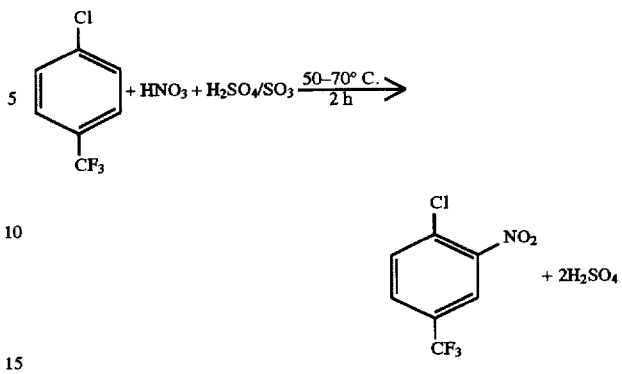

The molar ratio of nitric acid to 4-chlorotrifluoromethylbenzene starting material is at least 1:1 and more preferably, a slight excess of nitric acid is present to thereby insure substantially complete mononitration.

As the mononitration proceeds, 1 mol of nitric acid is consumed per mol of 4-chlorotrifluoromethylbenzene and as a result, 1 mol of water is produced. By providing a molar ratio of nitric acid to sulfur trioxide of at least 1:1, the liberated water is absorbed entirely by the sulfur trioxide, thereby forming additional sulfuric acid. The mononitration reaction is run at a temperature of approximately 20°–80° C. and most preferably from about 50°–55° C. After the dropwise addition of the 4-chlorotrifluoromethylbenzene the temperature of the reaction vessel may be gradually increased to 70° C. where it is maintained for approximately 2 hours under vigorous stirring. The temperature of the reaction vessel is then gradually reduced and ethylene dichloride is added to the reaction mixture.

The addition of this diluent and solvent provides a number of advantages. Specifically, it allows a more concentrated nitration mixture to be utilized. As a result, mononitration occurs faster and with better control over heat effects so as to substantially limit the formation of by-products such as 4-chlorobenzoic acid that would otherwise result from hydrolysis of the substrate.

The addition of ethylene dichloride also functions to eliminate the necessity of diluting the post nitration mixture with water as described in prior U.S. Pat. No. 4,096,195 to Schneider et al. As a result, it is no longer necessary to provide cooling to absorb the very significant heat of dilution that occurs in the prior art processes. Further, no diluted sulfuric acid waste is generated. In fact, the reaction product consists of an organic layer including the 4-chloro-3-nitrotrifluoromethylbenzene intermediate and a small percentage of organic impurities and by-products and a used acid layer.

In accordance with the present method, when the proper molar ratios are utilized and ethylene dichloride is added to enhance the separation of the desired mononitrated product and the organic impurities from the used acid layer, the used acid layer is substantially pure sulfuric acid. This acid may be enriched with sulfur trioxide ($SO_3$) to produce oleum which may be recycled in the process. This recycling not only minimizes the necessary waste treatment and handling procedures but also reduces overall processing costs by making more efficient and effective use of the raw materials. While ethylene dichloride is the preferred diluent and solvent for use in the separation following the first nitration step, it should be appreciated that other diluents and solvents may be utilized including, for example, methylene dichloride, chloroform, carbon tetrachloride and ethylene tetrachloride.

Following the mononitration and separation described above, the organic layer is collected and concentrated utilizing a rotary evaporator or any other appropriate means known to those skilled in the art. This allows the ethylene dichloride to be removed from the 4-chloro-3-nitrotrifluoromethylbenzene intermediate. Of course, the ethylene dichloride may be recycled in the process and utilized as the diluent and solvent in the separation of the next of batch of 4-chloro-3-nitrotrifluoromethylbenzene from 4-chlorotrifluoromethylbenzene mononitration.

Next, the mononitration product (4-chloro-3-nitro-trifluoromethylbenzene) intermediate is subjected to dinitration with a fresh nitric acid and oleum acid mixture. Preferably, the molar ratio of nitric acid to 4-chloro-3-nitrotrifluoromethylbenzene is at least 2:1 and, more preferably, at least 2.5:1 although a higher excess of nitric acid may be utilized. The excess nitric acid is provided so that the nitric acid present in the fresh acid mixture is sufficient to carry out not only the dinitration step presently being described but also may be recycled and utilized to complete the mononitration step previously described. Of course, as previously noted the molar ratio of nitric acid to sulfur trioxide is at least 1:1 in order to absorb the water generated during the dinitration and, following recycling, subsequent mononitration to which the acid mixture is applied.

Preferably, the dinitration is completed at a temperature of approximately 115° C. At this temperature, the 4-chloro-3-nitro-trifluoromethylbenzene intermediate from the mononitration is safely dinitrated to 4-chloro-3,5-dinitro-trifluoromethylbenzene within only approximately 4 hours.

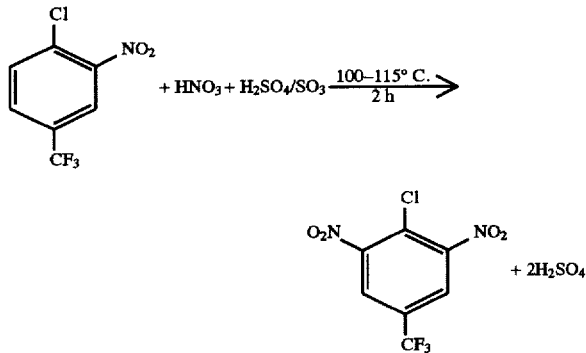

The product of the dinitration reaction consists of an organic layer including the desired 4-chloro-3,5-dinitro-trifluoromethylbenzene intermediate and a partially spent acid layer that is recycled back to the mononitration stage. Of course, the layers may be separated by any means known to those skilled in the art.

Following separation, and without any additional purification, the 4-chloro-3,5-dinitro-trifluoromethyl-benzene intermediate product of the dinitration stage is aminated with di-propylamine in order to produce 2,6-dinitro-N,N-dipropyl-4-(trifluoromethyl)-benzenamine, trifluralin.

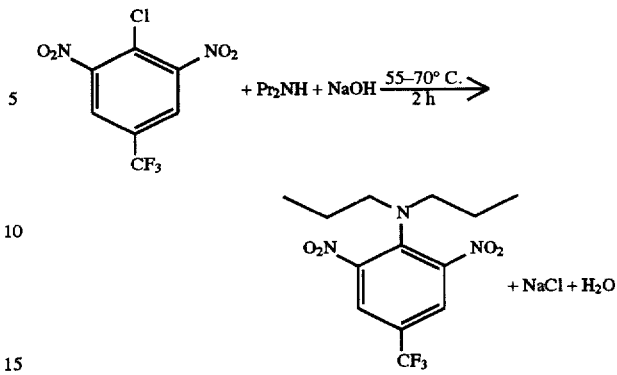

Specifically, the organic layer from the second nitration step including the 4-chloro-3,5-dinitrotrifluoromethylbenzene intermediate and small quantities of nitric acid, sulfuric acid and 4-chlorobenzoic acid and its nitro and dinitro derivatives is neutralized to a pH of approximately 7.5 utilizing 20% sodium hydroxide or other appropriate base. This is done in order to avoid excessive formation of nitrosoamine by-products during the amination procedure. Following pH adjustment, dipropylamine is added in parallel with sodium hydroxide. The resulting reaction is exothermic and the temperature during amination should be maintained so as not to exceed 70° C.

Next the post reaction mixture from the amination step is subjected to a simple evaporation of its volatile components. Specifically, the first condensate is collected at a temperature of approximately 86° C. (the boiling point of an azeotrope consisting of 83.8% dipropylamine and 16.2% water). This collected azeotrope may be recycled for utilization in the amination of the next batch to be processed. During the evaporation, the top part of the reactor is heated to approximately 115° C. in order to avoid any return of the vapors to the reactor. Also, an inert gas may be blown into the reactor in order to speed up the evaporation process.

The condensate of higher boiling point is collected in separate fractions and contains by-products and residual quantities of the substrate, the product and N-nitrosodipropylamine. The evaporation is carried on as long the concentration of the N-nitrosodipropylamine in the condensate fraction being collected is above the desired level, typically 0.5 ppm. Once the concentration of the N-nitrosodipropylamine in a collected fraction falls below 0.5 ppm, heating and stirring of the mixture is stopped to allow layer separation. The lower layer is the desired product, trifluralin which may be collected in drums or other vessel and allowed to crystallize.

Advantageously, the present process allows the production of trifluralin with a purity of up to 99.6% and nitrosoamines concentrations of less than 1 ppm and generally less than 0.5 ppm. The elimination of nitrosoamine from the trifluralin product is completed by a physical rather than a chemical process but without the utilization of saturated water steam distillation as taught in the prior art approach. Accordingly, no special equipment is required for steam production and a reactor of simpler design may be utilized. Of course, the recycling of the various reagents including the used sulfuric acid, ethylene dichloride and the dipropylamine also significantly improves the economy of the process.

The following synthesis and example is presented to further illustrate the invention, but it is not to be considered as limited thereto.

EXAMPLE

First Nitration

A two necked, 100 ml flask was equipped with a funnel, a thermometer and a magnetic stirring barr and placed in an oil bath preheated to 50° C. Into this flask, a mixture of acids from the second nitration step (described below) of an earlier experiment was introduced (~45 ml). Next, 18.05 g (0.1 mole, 13.34 ml) of 4-chlorotrifluoromethylbenzene (available from Aldrich Chemical Company, Inc. of Milwaukee, Wis., USA) was added dropwise, with intensive stirring over 20 minutes. At the addition time the temperature of the reaction mixture was kept on 55° C. (bath temperature 50° C.). After addition was completed the bath temperature was increased to 70° C. over the next 20 minutes and maintained for two more hours (all the time the reaction mixture was vigorously stirred). After that the bath temperature was decreased to 25° C. and when the contents of the flask reached 35° C., 50 ml of ethylene dichloride was added. Stirring of the mixture was maintained for 20 minutes then it was stopped and the mixture was left for 20 more minutes to afford layers separation. The lower layer of waste acids (3.5 g of nitric acid, 63 g of sulfuric acid and 0.4 g of the 4-chlorobenzoic, 4-chloro-3-nitrobenzoic and 4-chloro-3,5- dinitrobenzoic acids in ratio 89/5/6) was discarded while the upper organic layer was concentrated using a rotary evaporator (bath 50° C. at the vacuum of 25 mmHg) to separate product from ethylene dichloride. The residue quantities of ethylene dichloride were removed from the product by heating the product at 65° C. under reduced pressure of 25 mmHg. An oily light yellow product resulted comprising a mixture of 20.66 g of 4-chloro-3-nitrotrifluoromethylbenzene and 1.615 g of 4-chloro-3,5-dinitro-trifluoromethylbenzene. This mixture was used as a substrate in the second nitration step.

SECOND NITRATION

A two necked 100 ml round bottom flask was equipped with a dropping funnel, a thermometer and a magnetic stirrer and placed in an oil bath preheated to 80° C. Next, the nitration mixture composed of 15.94 g of 100% nitric acid (10.49 ml, 0.253 mole) and 52 g of 30% oleum (27 ml, d=1.925) was placed in the reactor and heated to 80° C. and vigorously stirred. Then a mixture of mononitro- and dinitrochlorotrifluoromethylbenzenes from the first nitration step (22.27 g) was added over a period of 15 minutes. After that time the temperature of the reaction mixture was increased to 110° C. over 20 minutes (bath temperature is also 110° C. at this time) and kept for one hour. The bath temperature was then increased to 115°–117° C. and maintained there for the next 2½ hours. The completion of the nitration was checked by gas chromatography. When the reaction was completed the temperature of the reacton mixture was decreased to 65° C. and stirring was turned off to allow layers separations. After approximately 30 minutes the lower-acids mixture layer was separated and recycled back for use in the first nitration step, while the upper layer of above 98% pure 4-chloro-3,5-dinitrotrifluoromethylbenzene (25.87 g) was used in the amination step.

AMINATION

A 150 ml round-bottomed, three neck flask was equipped with a dropping funnel, a thermometer, a reflux condenser and a magnetic stirrer and placed in an oil bath preheated to the temperature of 40° C. The flask was loaded with 20 ml of 1% sodium hydroxide and 25.87 g of 4-chloro-3,5-dinitro-trifluoromethylbenzene (crude) from the second nitration step. Stirring was then started and after 15 minutes the pH of the mixture was adjusted to 7.5 by addition of the required amount of 20% sodium hydroxide. Into the resulting mixture 11.4 g of dipropylamine was added (15.4 ml, 0.112 mole) in parallel with 19.0 ml of the 20% sodium hydroxide over a period of 25 minutes. At the end of addition the temperature of the reaction mixture was maintained at 60° C. for 2½ hours.

Next, 60 ml of water was added and the temperature of the bath was increased up to 120° C. while the dropping funnel was replaced by a distillation head equipped with a thermometer and a vapor condenser. The first condensate was collected at the temperature of 86° C.: that is, the boiling point of an azeotrope consisting of 83.8% dipropylamine and 16.2% water. The condensate of higher boiling point than that temperature was collected as a separate fraction. The evaporation was carried on until 70 ml of condensate was collected. Then, the evaporation was stopped and the contents of the reactor was checked for the presence of N-nitrosodipropylamine. The concentration was below 0.5 ppm.

At this time, the pH of the water layer was checked and adjusted to the pH 7.5–8.0 by addition of 20% sodium hydroxide. The reaction mixture was then left without stirring for approximately 30 minutes to allow layers separation. The lower layer of the 96+% pure trifluralin was than separated as an orange oil with a mp of 38°–40° C. in an amount of 30.9 g. After single crystallization from 27 ml of methyl alcohol (cooled to –0° C.) 26.9 g of the product with mp 47°–48° C. (99+% pure) was obtained. An additional 2.64 g of the product was obtained when the filtrate from crystallization was concentrated to the volume of 7.5 ml. Therefore, the final yield of the three stage process was 92.14%.

We claim:

1. A process for preparing 2,6-dinitro-N,N-dipropyl-4-(trifluoromethyl)benzenamine from 4-chlorotrifluoromethylbenzene, comprising:

(a) mononitrating 4-chlorotrifluoromethylbenzene substantially completely to 4-chloro-3-nitrotrifluoromethylbenzene with a mixture of nitric acid and oleum;

(b) separating said 4-chloro-3-nitrotrifluoromethylbenzene from waste acid mixture by adding ethylene dichloride;

(c) dinitrating said 4-chloro-3-nitrotrifluoromethylbenzene with a fresh mixture of nitric acid and oleum;

(d) separating said 4-chloro-3,5-dinitrotrifluoromethylbenzene from said mixture of nitric acid and oleum; and (e) aminating said 4-chloro-3,5-dinitrotrifluoromethylbenzene with dipropylamine to produce 2,6-dinitro-N,N-dipropyl-4-(trifluoromethyl) benzenamine.

2. The process of claim 1, further including distilling ethylene dichloride from said 4-chloro-3-nitrotrifluoromethylbenzene.

3. The process of claim 2, further including recycling distilled ethylene dichloride back to step (b).

4. The process of claim 1, further including evaporating volatile components directly from said 2,6-dinitro-N,N-dipropyl-4-(trifluoromethyl) benzenamine produced during said aminating step (e).

5. The process of claim 4, further including collecting unreacted dipropylamine during said evaporating step for recycling back into aminating step (e).

6. The process of claim 3, further including evaporating volatile components directly from said 2,6-dinitro-N,N-dipropyl-4-(trifluoromethyl) benzenamine produced during said aminating step (e).

7. The process of claim 6, further including collecting unreacted dipropylamine during said evaporating step for recycling back into aminating step (e).

8. The process of claim 1, further including recycling said mixture of nitric acid and oleum used in said dinitrating step (c) back into said mononitrating step (a).

9. The process of claim 1, further including adding sulfur trioxide to the waste acid mixture of said separating step (b) thereby regenerating the acid composition used in said dinitrating step (c).

10. A process for preparing 2,6-dinitro-N,N-dipropyl-4-(trifluoromethyl)benzenamine from 4-chlorotrifluoromethylbenzene, comprising:

(a) mononitrating 4-chlorotrifluoromethylbenzene substantially completely to 4-chloro-3-nitrotrifluoromethylbenzene with a mixture of nitric acid and oleum;

(b) separating said 4-chloro-3-nitrotrifluoromethylbenzene from waste acid mixture;

(c) dinitrating said 4-chloro-3-nitrotrifluoromethylbenzene with a fresh mixture of nitric acid and oleum;

(d) separating said 4-chloro-3,5-dinitrotrifluoromethylbenzene from said mixture of nitric acid and oleum; and (e) aminating said 4-chloro-3,5-dinitrotrifluoromethylbenzene with dipropylamine to produce 2,6-dinitro-N,N-dipropyl-4-(trifluoromethyl) benzenamine; and (f) evaporating volatile components directly from said 2,6-dinitro-N,N-dipropyl-4-(trifluoromethyl) benzenamine produced during said aminating step (e).

11. The process of claim 10, further including collecting unreacted dipropylamine during said evaporating step (f) for recycling back into said aminating step (e).

* * * * *